United States Patent [19]

Farrell

[11] Patent Number: 5,007,829
[45] Date of Patent: Apr. 16, 1991

[54] DENTAL ARTICULATOR APPARATUS

[76] Inventor: Frank C. Farrell, 18402 N. 70th Dr., Peoria, Ariz. 85345

[21] Appl. No.: 234,867

[22] Filed: Aug. 22, 1988

[51] Int. Cl.$^5$ ............................................. A61C 11/00
[52] U.S. Cl. ...................................... 433/61; 433/34; 433/57; 433/54; 433/64
[58] Field of Search ...................... 433/61, 62, 63, 64, 433/59, 60, 65, 57, 34, 67, 53; 249/54

[56] References Cited

U.S. PATENT DOCUMENTS

| | | | |
|---|---|---|---|
| 565,326 | 8/1896 | Bragg | 433/64 X |
| 2,200,058 | 5/1940 | Chott | 433/64 X |
| 2,365,475 | 12/1944 | Klein | 433/60 |
| 2,621,407 | 12/1952 | Schlesinger | 433/64 X |
| 2,765,533 | 10/1956 | McMorris | 433/64 |
| 2,928,175 | 3/1960 | Knoth | 433/60 |
| 3,019,529 | 2/1962 | Hinze | 433/62 X |
| 3,161,917 | 12/1964 | Wiland | 249/54 |
| 4,200,981 | 5/1980 | Fine | 433/60 |
| 4,378,929 | 4/1983 | Huffman | 249/54 X |
| 4,481,162 | 11/1984 | Huffman | 249/54 X |
| 4,494,934 | 1/1985 | Huffman | 249/54 X |
| 4,496,320 | 1/1985 | Hwang et al. | 433/60 |
| 4,538,987 | 9/1985 | Weissman | 433/60 |
| 4,548,581 | 10/1985 | Huffman | 433/64 |
| 4,797,097 | 1/1989 | Cohn | 433/61 X |
| 4,842,242 | 6/1989 | Huffman | 433/54 X |

FOREIGN PATENT DOCUMENTS

| | | | |
|---|---|---|---|
| 572850 | 11/1958 | Belgium | 433/64 |
| 64042 | 1/1944 | Denmark | 433/64 |
| 460748 | 12/1913 | France | 433/64 |
| 974950 | 2/1951 | France | 433/61 |

Primary Examiner—John G. Weiss
Assistant Examiner—Nicholas D. Lucchesi
Attorney, Agent, or Firm—David G. Rosenbaum

[57] ABSTRACT

A dental articulator principally having a posterior articulating assembly, an anterior incisal support assembly and a mold assembly. The posterior articulating assembly is characterized by a ball and socket joint and a pivot joint. The ball and socket joint has a socket member which is operably coupled to the pivot joint and a ball member which is operably coupled to a first teeth cast. The pivot joint has a pivot member operably coupled to a support member for joining the pivotal joint to a second teeth cast. The anterior incisal support assembly has an incisal pin operably joined to the first teeth cast and an incisal plate, which cooperates with the incisal pin, joined to the second teeth cast. The mold assembly has a plurality of molds each having an aperture in each of an anterior and posterior portion of the mold and an associated alignment protrusion, in close proximity to the aperture, for aligning joining members, to be cast into the first and second teeth casts, for connecting the first and second teeth casts to the ball member and the support member.

10 Claims, 2 Drawing Sheets

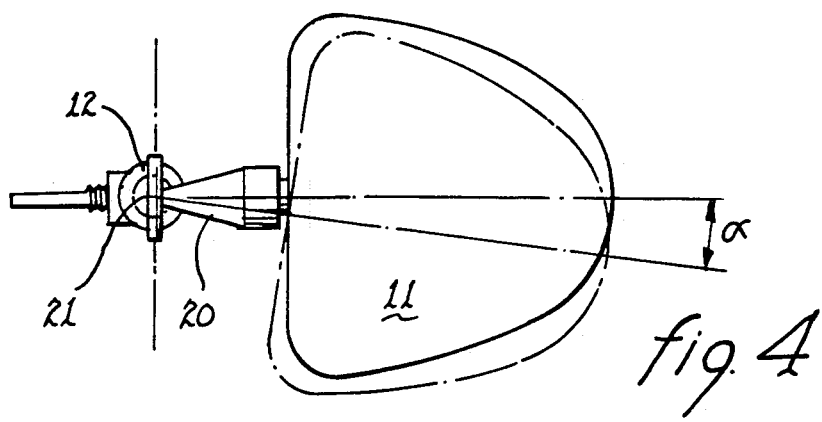
fig. 4
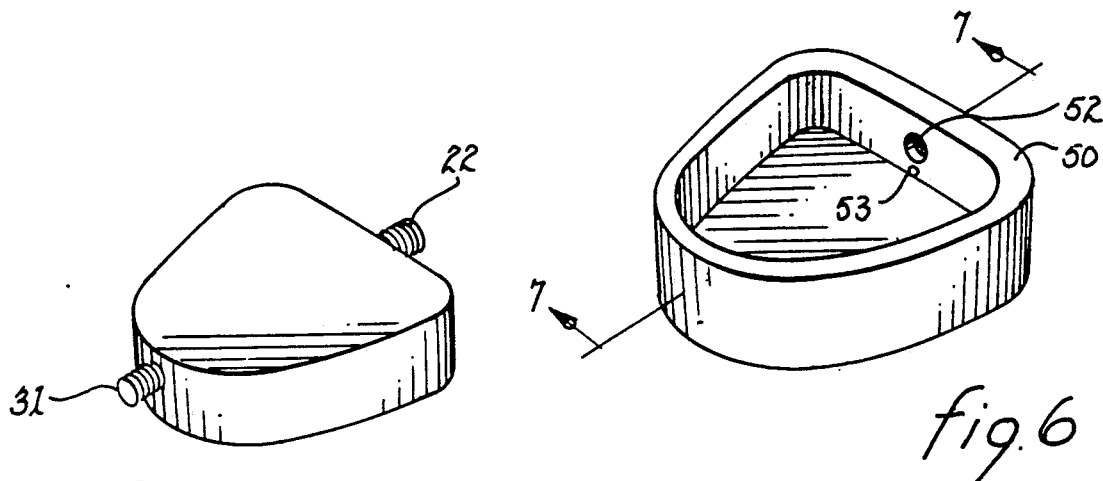
fig. 5
fig. 6
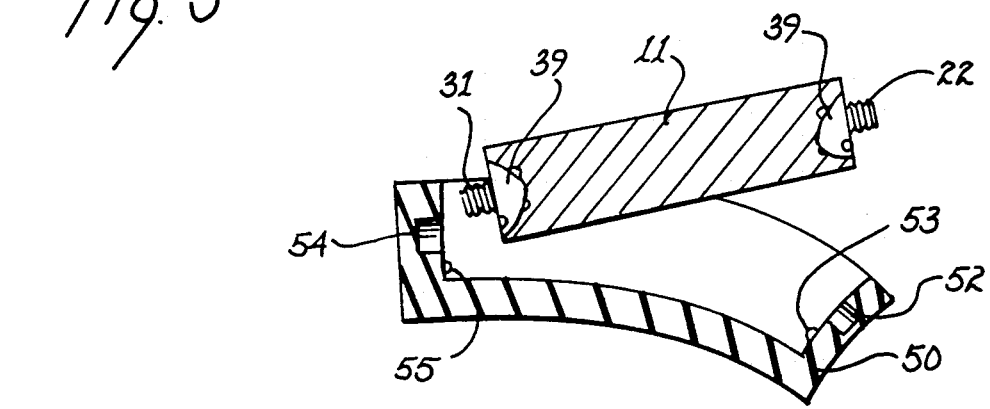
fig. 7
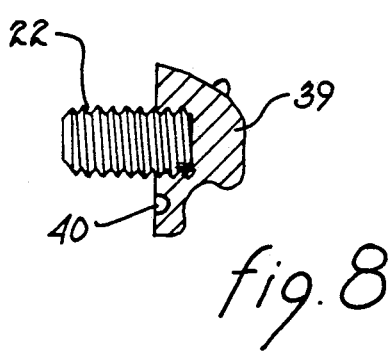
fig. 8

DENTAL ARTICULATOR APPARATUS

BACKGROUND OF THE INVENTION

This invention relates generally to dental articulators utilized by dental technicians to fabricate full or partial dental prosthetics according to specifications established by a dentist. More particularly, the present invention relates to an improved dental articulator incorporating novel means for providing a wide range of adjustment of the mandibular and maxillary casts to more accurately replicate the natural ranges of motion of the human mouth.

In forming dental prosthetics, such as dentures, molds of a patient's mouth are used to create plaster casts of the patient's mandibular and maxillary teeth. It is important that the patient's natural bite be replicated in order to form a well-fitting dental prosthesis. The function of a dental articulator is to secure a mandibular cast and a maxillary cast in a device which replicates the patient's natural bite and alignment between the maxillary and mandibular teeth. During the biting and grinding motions associated with mastication, a number of vertical, lateral and posterior-anterior mandibular displacements occur. It is necessary, therefore, that the dental articulator be minimally capable of cast movement in the vertical, lateral and posterior-anterior axes.

Past attempts to replicate proper anatomical movement of the mandibular cast relative to the maxillary cast have resulted in elaborate, complex and expensive dental articulators. Exemplary of such prior art dental articulators are those disclosed in U.S. Pat. No. 3,019,529 issued Feb. 6, 1962 to G. Hinze, entitled "Dental Articulator"; U.S. Pat. No. 3,359,639 issued Dec. 26, 1967 to N. F. Guichet entitled "Dental Articulators and Clutch Fabrication"; U.S. Pat. No. 3,590,487 issued July 6, 1971 to N. F. Guichet entitled "Dental Articulator"; U.S. Pat. No. 4,163,319 issued Aug. 7, 1979 to G. Ouaknine entitled "Dental Occluder"; and U.S. Pat. No. 4,305,708 issued Dec. 15, 1981 to R. Beu entitled "Dental Articulator". Each of these prior art dental articulators are characterized by a mandibular and maxillary stage. Typically, the mandibular stage has a pair of adjacent vertical supports, across which the maxillary stage is operably supported and capable of articulatory movement. The mandibular and maxillary casts are retained by their respective stages through various attachment means which secure the maxillary mold from a superior position and the mandibular mold from an inferior position. The prior art devices are characterized by having an assembly, often adjustable, for clamping the maxillary mold from a superior position and suspending the maxillary mold from the maxillary stage. Associated with the clamping assembly is typically a mandibular cast support assembly, which is also often adjustable, associated with the mandibular stage.

Due principally to these rather complex structural arrangements, there is an overabundance of adjustment points to secure the maxillary and mandibular casts within the articulator. These complex joints require the dental technician to make a myriad of fine bilateral adjustments in order to replicate the simplest displacement in a patient's bite. Moreover, within the simulated mouth, access to the work area is impaired by the articulator structure thereby increasing the difficulty of forming a well-fitting prosthesis. Further, each of the prior art articulators have complex mechanical arrangements for the mandibular joint to replicate the arcuate movement of the mandibular stage with respect to the maxillary stage.

Because of the prevalent need for affordable well-fitted dental prosthesis, a less complex, easier to use and relatively inexpensive dental articulator is provided by the present invention. The dental articulator of the present invention remedies the problems of the prior art dental articulators by providing a dental articulator which increases ease of access to the work area and requires minimum adjustment to replicate natural full range of motion of the human mouth, including naturally occurring vertical, lateral and anterior-posterior displacements. The novel dental articulator remedies the deficiencies in the prior art by utilizing posterior mold attachments in conjunction with a novel arrangement of a ball joint and a pivot joint.

SUMMARY OF THE INVENTION

It is, therefore, an object of this invention to provide an improved means for fabricating full or partial mandibular and maxillary dental molds.

It is also an object of the present invention to provide an improved means for mounting full or partial mandibular and maxillary dental molds in a dental articulator.

It is another object of the present invention to provide an improved dental articulator apparatus, including full and partial mandibular and maxillary molds, which is characterized by ease of use, ease of adjustment and capability of replicating the full range of motion of the human mouth.

It is yet another object of the present invention to provide an improved dental articulator having posterior mold attachments, a ball joint and a pivot joint and means for raising and lowering the dental molds within the dental articulator.

These and other objects, features and advantages of the present invention will become more apparent, to those skilled in the art, from the following more detailed description of the preferred embodiment of the invention with reference to the accompanying drawings in which like features are identified by like reference numerals.

BRIEF DESCRIPTION OF THE DRAWINGS

FIG. 4 is a top elevational view of the dental articulator apparatus according to the present invention and an associated maxillary cast.

FIG. 5 is a perspective view of a cast and associated connection members of the dental articulator apparatus according to the present invention.

FIG. 6 is a perspective view of a mold for making a mandibular or maxillary cast according to the present invention.

FIG. 7 is a side elevational, partial cross-sectional view taken along line 7—7 of FIG. 6.

FIG. 8 is a side elevational, partial cross-sectional view of a connection member and associated cast plug of the dental articulator apparatus according to the present invention.

DETAILED DESCRIPTION OF THE PREFERRED EMBODIMENT

Figure 1:
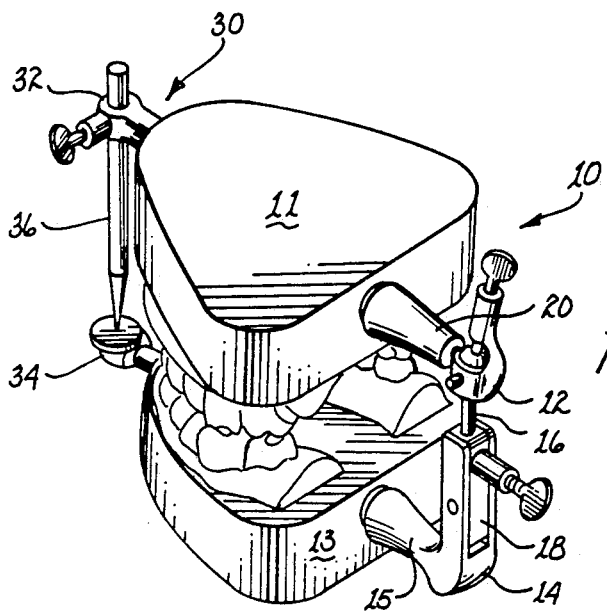
FIG. 1 is a perspective view of a dental articulator apparatus according to the present invention and associated maxillary and mandibular casts.
Figure 2:
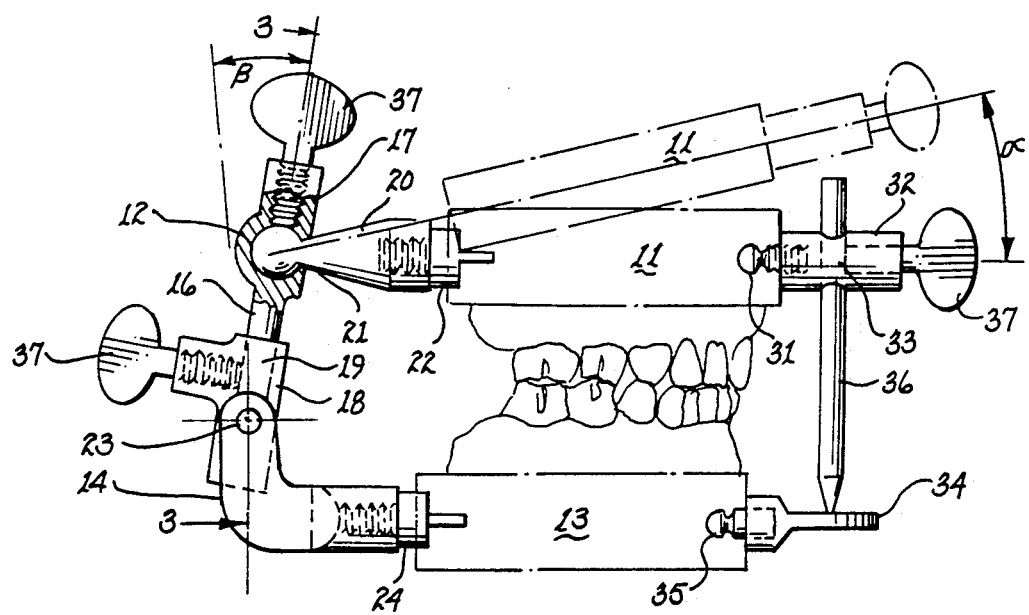
FIG. 2 is a side elevational, partial cross-sectional view of the dental articulator apparatus according to the present invention and associated maxillary and mandibular casts.

In FIGS. 1 and 2 there is shown a dental articulator apparatus 10 in accordance with the preferred embodiment of the present invention. Common to virtually all dental articulators is either a full or partial maxillary cast 11 and mandibular cast 13 of the dental patient's teeth. While the full casts are illustrated in the accompanying figures, it will be appreciated, by those skilled in the art, that partial casts are intended to be included as falling within the ambit of the preferred embodiment of the present invention.

The dental articulator apparatus 10 of the present invention consists of three groups of discrete cooperating assemblies. As best illustrated with reference to FIGS. 2, 3 and 4, a posterior articulating assembly is provided which consists generally of a maxillary support member 20 and a mandibular support member 15. Maxillary support member 20 and mandibular support member 15 removably couple to each of the maxillary cast 11 and mandibular cast 13, respectively. Maxillary support member 20 removably couples to maxillary cast 11 by means of a first posterior joining member 22 which removably couples to one end of maxillary support member 20. Mandibular support member 15 removably couples to mandibular cast 13 by means of a second posterior joining member 24. Maxillary support member 20 has a ball member 21 disposed on an end opposite to the one end of the maxillary support member which removably couples to the first posterior joining member. A socket member 12 operably couples to ball member 21 in freely rotatable fashion as a ball and socket joint. Socket member 12 has a stem member 16 extending downwardly therefrom.

To insure proper alignment of the maxillary cast 11 with respect to the mandibular cast 13, it is necessary to control the free rotation of the ball member 21 within the socket member 12. According to the preferred embodiment of the present invention there is provided a set screw 37 which screwably couples to socket member 12 by an internally threaded portion of socket member 12. The internally threaded portion of socket member 12 permits the set screw 37 to frictionally contact the ball member 21 thereby locking a desired position of maxillary cast 11. It will be appreciated, by those skilled in the art, that alternative means for controlling the rotation of the ball member 21 within socket member 12 are possible. For example, a series of cooperating detents may be disposed within the inner surface of socket member 12 and about the outer surface of ball member 21 which frictionally control movement of ball member 21 within socket member 12.

Figure 3:
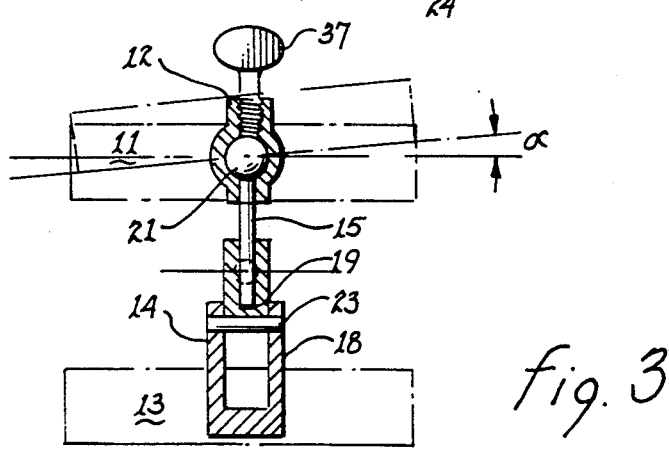
FIG. 3 is a rear elevational, partial cross-sectional view taken along line 3—3 of FIG. 2.

By providing the ball and socket joint for the maxillary cast, it is possible for the dental technician to move maxillary cast 11 vertically through an angle α in FIG. 2, adjust the attitude of maxillary cast 11 through angle β in FIG. 3 and horizontally through angle δ in FIG. 4 to adjust the position of maxillary cast 11 as appropriate for the individual patient's bite. Upon determining the proper position of the maxillary cast, the dental technician will lock the ball and socket joint by tightening set screw 37 thereby frictionally engaging ball member 21 within socket member 12 and setting the position of maxillary cast 11 at an angle α, β or δ.

Mandibular support member 15 has a generally L-shaped configuration wherein the horizontal leg portion of the L-shaped configuration removably couples to the second posterior joining member 24. Mandibular support member 15 further has a slotted upright portion 14 forming the upper aspect of the generally L-shaped configuration. A pivot member 18 is disposed within the slotted upright portion 14 and is secured within the slotted portion by a pintle 23. Pintle 23 passes laterally through an upper portion of the pivot member 18 and the slotted upright portion 14 and operably secures pivot member 18 within the slotted upright portion 14 of the mandibular support member 15.

Pivot member 18 further has a longitudinally disposed bore 19 passing therethrough adapted to operably receive stem member 16 of the socket member 12. Stem member 16 may be reciprocally adjusted within bore 19 of pivot member 18 to further permit vertical adjustment of the alignment between maxillary cast 11 and mandibular cast 13.

In order to secure stem member 16 within bore 19 in a locked position, it is desirable, according to the preferred embodiment of the present invention, to provide a set screw 37 which operably engages a female threaded portion of pivot member 18 and permits the set screw 37 to frictionally contact the stem member 16 of the socket member 12. It will be appreciated, by those skilled in the art, that alternative means for controlling the reciprocal movement of stem member 16 of the pivot member 18 within bore 19 are contemplated and within the scope of the present invention. For example, a series of cooperating detents may be disposed within the inner surface of bore 19 and about the outer surface of stem member 16 which frictionally control the reciprocal movement of the stem portion 16 within bore 19 and permit the step portion to be frictionally secured at a desired position within bore 19.

It will be appreciated, by those skilled in the art, that pivot member 18 is able to freely pivot in a plane perpendicular to the plane of the mandibular support member 15 and the maxillary support member 13 and permit the opening and closing thereof. Thus, the articulating assembly of the dental articulation apparatus of the present invention has been identified and described as the posterior portion of the dental articulator apparatus of the present invention.

The second discrete assembly consists of a anterior incisal assembly. The purpose of the anterior incisal assembly is to maintain a vertical support at the frontal section of the maxillary cast 11 and mandibular cast 13. Anterior assembly consists of an incisal pin 36, and incisal pin support 32 having a vertical bore 33 passing therethrough for reciprocally accommodating the incisal pin 36 therein, and an incisal plate 34 for cooperating with the incisal pin 36 and supporting the incisal pin 36 thereupon. Incisal pin support 32 is removably coupled to maxillary cast 11 by means of a first anterior joining member 31 which is embedded into the anterior portion of the maxillary cast 11 during the molding procedure. Incisal plate 34 is also removably coupled to mandibular cast 13 by means of a second anterior joining member 35 which is embedded into the anterior portion of the mandibular cast 11 during the molding procedure. It will be understood, by those skilled in the relevant art, that the posterior articulating assembly and the anterior incisal assembly cooperate to support the maxillary cast 11 and the mandibular cast 13 in a position which accurately replicates the patient's bite while facilitating easy access to the working area within the dental articulator apparatus.

A final discrete assembly consists of the mold assembly, depicted in FIGS. 5-8, which is used to create the maxillary cast 11 and set the first posterior joining member 22 and first anterior joining member 31 into the maxillary cast 11, as well as to create the mandibular cast 13 and set the second posterior joining member 24 and second anterior joining member 35 into the mandibular cast. According to the preferred embodiment of the present invention, and with particular reference to FIG. 8, each of first and second posterior joining members 22, 24, as well as each of first and second anterior joining members 31, 35, are threaded members having an alignment head 39 associated therewith. Alignment head 39, which may be formed of any suitable plastic material capable of being bonded within the plaster casting material used to make maxillary cast 11 and mandibular cast 13, has an detent 40 which permits a proper orientation of the threaded member within the mold 50 in FIG. 7.

When threaded members are employed for each of first and second posterior joining members 22, 24, as well as each of first and second anterior joining members 31, 35, it is necessary to set the threaded member in a proper orientation. To ensure that the maxillary cast 11 and the mandibular cast 13 are horizontally oriented when joined to the maxillary support member 20 and mandibular support member 15, respectively, an anterior alignment protrustion 55 and posterior alignment protrustion 53 are integrally disposed on an inner surface of mold 50 and in anterior and posterior positions, respectively. Immediately superior to each of the anterior alignment protursion 55 and posterior alignment protrusion 53 are anterior aperture 54 and posterior aperture 52 which receive either first or second posterior joining member 22, 24, and a corresponding one of first or second anterior joining member 31, 35, prior to casting. After insertion of one of first or second posterior joining member 22, 24, and a corresponding one of first or second anterior joining member 31, 35, the alignment head 39 is adjusted so that alignment protrusion 53 or 55 engages detent 40 in alignment head 39 thereby properly positioning the joining member in the mold 50.

After casting a maxillary cast 11 or a mandibular cast 13, the threads of the joining members 22 and 31 are properly oriented so that connection of the joining member 22 to maxillary support member 20 results in a proper horizontal orientation for maxillary cast 11. Moreover, connection of joining member 31 to incisal pin support member 32 results in a proper vertical orientation of incisal pin 36.

It will be understood and appreciated, by those skilled in the art, that alternative fitting types, e.g. bayonet fittings, compression fittings, etc., may be employed as the first and second posterior joining members 22, 24 or as the first and second anterior joining members 31, 35. Where such non-threaded members are employed, they are typically self-aligning, thereby eliminating the need for the alignment head 39, detent 40 and alignment protrusions 53 and 55.

While the invention has been particularly shown and described in reference to the preferred embodiments thereof, it will be understood by those skilled in the art that changes in form and details may be made without departing from the spirit and scope of the invention. For example, the dental articulator apparatus may be made of a plastic or metal material, alternative securing means for the ball and socket joint and reciprocating socket member may be employed or alternative joining means for joining the casts to the articulator may be used and still fall within the scope and content contemplated by the present invention.

I claim:

1. A dental articulator apparatus, comprising:
    a ball joint having a ball member and a socket member, said ball member having an associated first joining means for removably coupling said ball member to a posterior aspect of a first teeth cast and said socket member further having a socket portion, a downwardly extending stem portion and first securing means for controlling movement of said ball member within said socket member;
    second joining means for removably coupling to a posterior aspect of a second teeth cast said second joining means comprising a substantially L-shaped member having upstanding co-planar members defining a vertical slot therebetween, a pintle member disposed horizontally across said vertical slot and supported by said upstanding co-planar members and a substantially horizontal leg portion adapted to removably couple to the second teeth cast; and
    a pivot member, pivotally coupled to said pintle member, having an internal bore adapted to reciprocally receive said downwardly extending stem portion of said socket member and second securing means for securing said downwardly extending stem portion.

2. The dental articulator apparatus according to claim 1, wherein said first joining means further comprises an internally threaded end portion.

3. The dental articulator apparatus according to claim 1, wherein said first joining means and said second joining means further comprise a nonthreaded coupling fitting.

4. The dental articulator apparatus according to claim 1, wherein said first serving means further comprises an internally threaded portion extending outwardly from said socket portion and an externally threaded screw member receivably coupled within said internally threaded portion.

5. The dental articulator apparatus according to claim 1, wherein said substantially horizontal leg portion further comprises an internally threaded end portion which is removably coupled to the second teeth cast.

6. The dental articulator apparatus according to claim 1, wherein said apparatus further comprises incisal support means having an incisal pin operably coupled to an anterior portion of the first teeth cast and an incisal plate coupled to an anterior portion of the second teeth cast.

7. A dental articulator apparatus, comprising:
    a ball joint having a ball member and a socket member, said ball member further having an associated first joining means for removably coupling said ball member to a first teeth cast;
    second joining means for removably coupling to a second teeth cast at one end thereof;
    means for operably coupling said second joining means to said ball joint and allowing articulation between said first joining means and said second joining means;
    a plurality of teeth molds, each teeth mold having apertures disposed in an anterior portion and a posterior portion of said teeth mold, wherein each of said plurality of teeth molds further comprises an alignment protrusion in close proximity to each of said apertures disposed in the anterior and posterior portion of said teeth mold; and a plurality of externally threaded joining members, one of said plurality of externally threaded joining members being disposed in said apertures in the anterior portion and posterior portion of said teeth mold, wherein each of said plurality of externally threaded joining members further comprises a head member having a detent in close proximity to an externally threaded portion of said externally threaded joining member, said detent being aligned with said alignment protrusion in close proximity to said aperture in an anterior or posterior position in said teeth mold, thereby properly orienting said externally threaded portion within said teeth mold such that the first or second teeth cast has a horizontal alignment when operably coupled to the dental articulator apparatus.

8. A dental articulator apparatus, comprising:

a ball joint having a ball member and a socket member, said ball member further having an associated first joining means for removably coupling said ball member to a first teeth cast, said socket member having a socket portion, a stem portion and securing means for controlling movement of said ball member within said socket member;

second joining means for removably coupling to a second teeth cast at one end thereof, said second joining means having a slotted upper portion and a lower portion adapted to couple to the second teeth cast;

pivot means having an internal bore for reciprocally receiving said socket member therein and operably coupling to and pivoting relative to said second joining means;

incisal support means having an incisal pin operably coupled to an anterior portion of the first teeth cast and an incisal plate coupled to an anterior portion of the second teeth cast;

a plurality of teeth molds, each teeth mold having apertures disposed in an anterior portion and a posterior portion of said teeth mold, wherein each of said plurality of teeth molds further comprises an alignment protrusion in close proximity to each of said apertures disposed in the anterior and posterior portion of said teeth mold; and a plurality of externally threaded joining members, one of said plurality of externally threaded joining members being disposed in each of said apertures in the anterior portion and posterior portion of said teeth mold, wherein each of said plurality of externally threaded joining members further comprises a head member having a detent in close proximity to an externally threaded portion of said externally threaded joining member, said detent being aligned with said alignment protrusion in close proximity to said aperture in an anterior or posterior portion in said teeth mold, thereby properly orienting said externally threaded portion within said teeth mold such that the first or second teeth cast has a horizontal alignment when operably coupled to the dental articulator apparatus.

9. The dental articulator apparatus according to claim 8, wherein said first joining means further comprises an internally threaded end portion.

10. The dental articulator apparatus according to claim 8, wherein said lower portion of said second joining member further comprises an internally threaded end portion which removably couples to the second teeth cast.

* * * * *

UNITED STATES PATENT AND TRADEMARK OFFICE
CERTIFICATE OF CORRECTION

PATENT NO. : 5,007,829
DATED : April 16, 1991
INVENTOR(S) : Frank C. Farrell

It is certified that error appears in the above—identified patent and that said Letters Patent is hereby corrected as shown below:

In Claim 4, column 6, line 39, delete "serving", and insert therefor --securing--.

Signed and Sealed this

Eighteenth Day of August, 1992

Attest:

DOUGLAS B. COMER

Attesting Officer

Acting Commissioner of Patents and Trademarks